United States Patent [19]

Scholz

[11] Patent Number: 5,587,517
[45] Date of Patent: Dec. 24, 1996

[54] PROCESS FOR THE PREPARATION OF CHLOROPHENYLPHOSPHANES

[75] Inventor: Guido Scholz, Köln, Germany

[73] Assignee: Hoechst Aktiengesellschaft, Frankfurt am Main, Germany

[21] Appl. No.: 332,909

[22] Filed: Nov. 1, 1994

Related U.S. Application Data

[63] Continuation-in-part of Ser. No. 147,331, Nov. 3, 1993, abandoned.

[30] Foreign Application Priority Data

Nov. 17, 1992 [DE] Germany .................... 42 38 711.6

[51] Int. Cl.$^6$ .................................................. C07F 9/52
[52] U.S. Cl. ................................................... 568/16
[58] Field of Search .................................... 568/16

[56] References Cited

U.S. PATENT DOCUMENTS 4,521,347  6/1985  Kleiner .

Primary Examiner—Johann Richter
Assistant Examiner—John Peabody
Attorney, Agent, or Firm—Connolly & Hutz

[57] ABSTRACT

Preparation of chlorophenylphosphanes of the formula $$(C_6H_5)_n PCl_{3-n}$$

in which n is 1 or 2, triphenylphosphane $(C_6H_5)_3P$ and phosphorus trichloride $PCl_3$ are reacted at temperatures above 300° C., for which liquid triphenylphosphane and gaseous phosphorus trichloride are introduced in a molar ratio of 1:(3 to 12) at the upper end of a vertically arranged, elongated and heated reaction zone. The reaction product discharged at the lower end of the reation zone is transferred to a residence zone charged with phosphorus pentachloride. Finally, the excess phosphorus trichloride is removed from the reaction product, via a subsequent fractionating zone, by heating the residence zone with the resultant formation of a $PCl_3$-depleted reaction product. The substances contained in the $PCl_3$-depleted reaction product are separated from one another by fractionated rectification under reduced pressure.

5 Claims, 1 Drawing Sheet

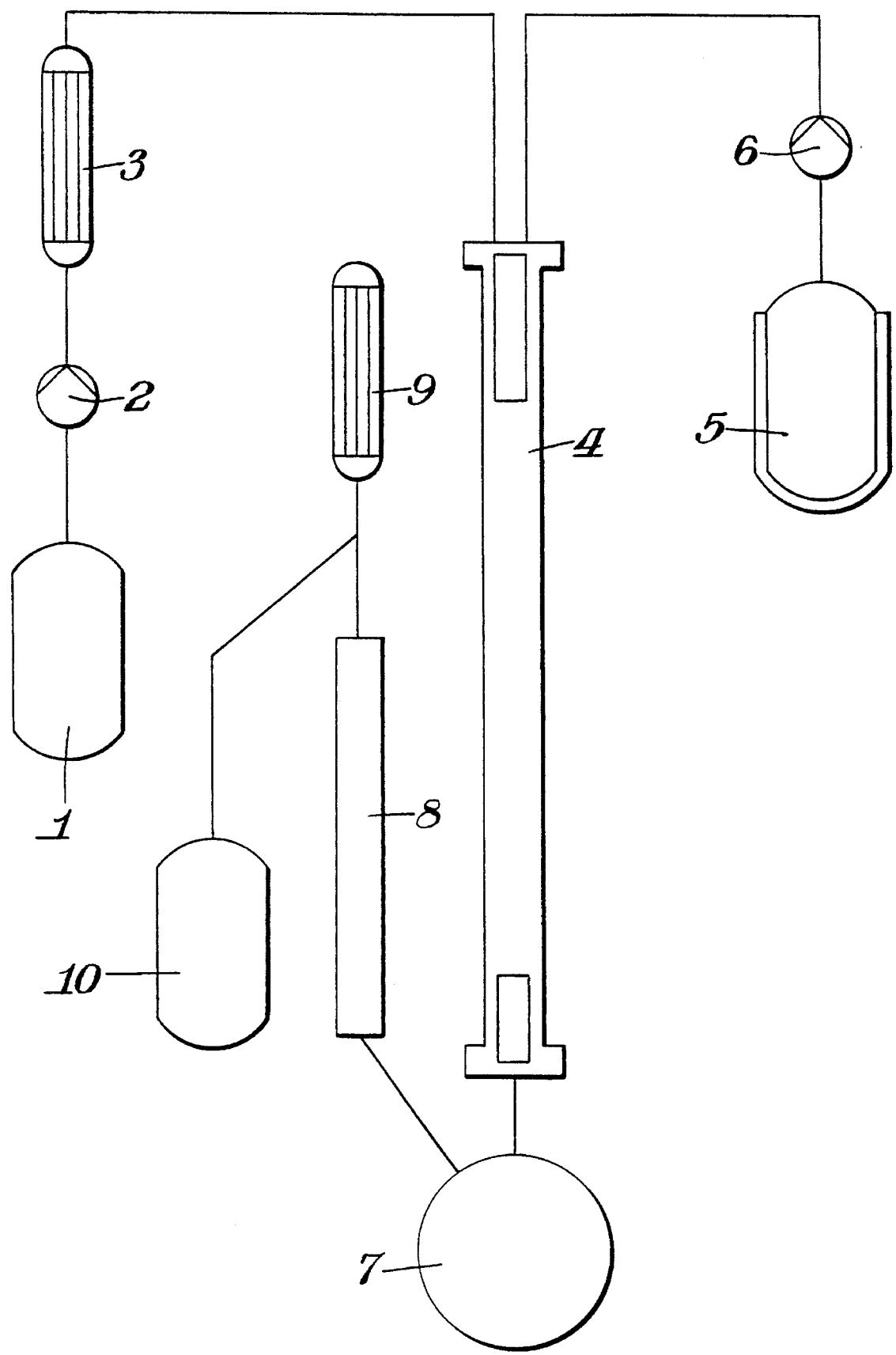

PROCESS FOR THE PREPARATION OF CHLOROPHENYLPHOSPHANES

This is a continuation-in-part application of Ser. No. 08/147,331 filed Nov. 3, 1993, now abandoned.

FIELD OF THE INVENTION

The present invention relates to a process for the preparation of chlorophenylphosphanes of the formula $$(C_6H_5)_n PCl_{3-n}$$

in which n is 1 or 2, by reaction of triphenylphosphane $(C_6H_5)_3P$ and phosphorus trichloride $PCl_3$ at temperatures above 300° C.

BACKGROUND AND PRIOR ART

A process for the preparation of a mixture of dichlorophenylphosphane $C_6H_5PCl_2$ and chlorodiphenylphosphane $(C_6H_5)_2 PCl$ in which triphenylphosphane $(C_6H_5)_3P$ and phosphorus trichloride $PCl_3$ are reacted at temperatures of 320° to 700° C. in an autoclave or in a quartz tube in an electric furnace is known from U.S. Pat. No. 4,521,347.

The disadvantage of the known process is that the reaction product contains white phosphorus, which makes working up of the reaction product by distillation very difficult.

SUMMARY OF THE INVENTION

The object of the present invention is therefore to provide a process for the preparation of chlorophenylphosphanes by reaction of triphenylphosphane and phosphorus trichloride at a molar ratio of 1:(3 to 12) at temperatures above 300° C. in which the reaction product obtained is free from white phosphorus. This is achieved according to the invention by introducing liquid triphenylphosphane and gaseous phosphorus trichloride in a molar ratio between 1 to $\geq 2$ and $\geq 2$ to 1 at the upper end of a vertically arranged, elongated and heated reaction zone; by transferring the reaction product discharged at the lower end of the reaction zone to a residence zone charged with phosphorus pentachloride; and by removing the excess phosphorus trichloride from the reaction product, via a subsequent fractionating zone, by heating the residence zone.

DESCRIPTION OF THE PREFERRED EMBODIMENTS

The process according to the invention furthermore can optionally also be carried out such that a) the reaction zone is filled at least 50% of its length with a bulk material comprising granular silicon carbide;
b) regions in the reaction zone near its upper and lower ends are free from bulk material;
c) the silicon carbide of the bulk material has particle sizes of 2 to 8 mm;
d) the silicon carbide of the bulk material has particle sizes of 3 to 6 mm;
e) the reaction zone in the region of the silicon carbide bulk material has temperatures of 350° to 650° C.;
f) the reaction zone in the region of the silicon carbide bulk material has temperatures of 500° to 600° C.;
g) the reaction zone comprises an electrically heatable silicon/silicon carbide tube.

The reaction product obtained by the process according to the invention evidently contains no white phosphorus because it has reacted with the phosphorus pentachloride in the residence zone.

DESCRIPTION OF THE DRAWING

The attached drawing shows in a diagram form a plant suitable for carrying out the process of the invention.

Liquid phosphorus trichloride is fed from a reservoir 1 by a first pump 2 to an evaporator 3 which is joined in the direction of flow to the upper end of a vertically arranged electrically heatable tube 4 made of silicon/silicon carbide. Tube 4 has a length of 2000 mm and an inner diameter of 50 mm. Tube 4 is partially filled with granular silicon carbide (particle sizes: 3 to 6 mm), wherein an area of 470 mm from the upper end of tube 4 and an area of 230 mm from the lower end of tube 4 are free from granular silicon carbide. Liquid triphenylphosphane is also metered from a tank 5, provided with a heating jacket, via a second pump 6 into the upper end of tube 4. The reaction product discharged from the lower end of the tube 4 passes into a residence tank 7, which is provided with a heating device and contains phosphorus pentachloride. The contents of the residence tank 7 are kept at a temperature between 80° and 115° C., the phosphorus trichloride flowing out of the residence tank 7 in gaseous form being distilled off over a column 8, liquefied in a condenser 9 and collected in a tank 10.

EXAMPLE 1

(Comparison Example)

2051 g (14.9 mol) of $PCl_3$ were metered from a reservoir 1 (cf. the drawing) with the aid of a first pump 2 into an evaporator 3 in the course of 3 hours. The gaseous $PCl_3$ flowing out of the evaporator 3 entered a vertically arranged tube 4, which was made of silicon/silicon carbide and was heated electrically at 590° C. and which contained a bulk material comprising silicon carbide (particle size about 4 mm). At the same time, 816 g (3.11 mol) of liquid $Ph_3P$ were introduced from a tank 5, provided with a heating jacket, via a second pump 6 into the upper end of the tube 4. The reaction product collecting in a residence tank 7 was kept at a temperature of at least 80° C. in this tank, which meant that a large proportion of the excess $PCl_3$ distilled off over a column 8, and was liquefied in a condenser 9 and collected in a tank 10.

The fractionated rectification at 9 to 13 mbar of the $PCl_3$-depleted reaction product withdrawn from the residence tank 7 gave the following substances, in addition to further unreacted $PCl_3$:

1284 g (7.2 mol) of $PhPCl_2$
250 g (1.1 mol) of $Ph_2PCl$
86.7 g (0.77 mol) of $PhCl$
3.3 g (27 mmol) of $P_4$
37.7 h (144 mmol) of $Ph_3P$

EXAMPLE 2

(Comparison Example)

Example 1 was repeated with the modifications that the tube 4 was heated electrically at 580° C. and that 800 g (3.05 mol) of liquid $Ph_3P$ were introduced into the top of the tube 4. The fractionated rectification at 9 to 13 mbar of the $PCl_3$-depleted reaction product withdrawn from the residence tank 7 gave the following substances, in addition to further unreacted $PCl_3$:

1189 g (6.6 mol) of $PhPCl_2$
261 g (1.2 mol) of $Ph_2PCl$
64.4 g (0.57 mol) of PhCl
2.2 g (18 mmol) of $P_4$
65.8 g (0.25 mol) of $Ph_3P$

EXAMPLE 3

(Comparison Example)

Example 1 was repeated with the modifications that the tube 4 was heated electrically at 600° C., that 2905 g (21.2 mol) of $PCl_3$ were metered into the evaporator 3 and that 504 g (1.92 mol) of $Ph_3P$ were introduced into the top of the tube 4. The fractionated rectification at 9 to 13 mbar of the $PCl_3$-depleted reaction product withdrawn from the residence tank 7 gave the following substances, in addition to further unreacted $PCl_3$:

690 g (3.9 mol) of $PhPCl_2$
46 g (0.21 mol) of $Ph_2PCl$
86.6 g (0.77 mol) of PhCl
4.3 g (35 mmol) of $P_4$
<0.1 g of $Ph_3P$

EXAMPLE 4

(Comparison Example)

Example 1 was repeated with the modifications that tube 4 does not contain any bulk materials.

The fractionated rectification at 9 to 13 bar of the $PCl_3$-depleted reaction product withdrawn from the residence tank 7 gave to following substances, in addition to further unreacted $PCl_3$:

181 g (1.01 mol) of $PhPCl_2$
53 g (0.24 mol) of $Ph_2PCl$
14.2 g (0.126 mol) of PhCl
1.3 g (10.5 mmol) of $P_4$
676 g (2.58 mol) of $Ph_3P$

EXAMPLE 5

(according to the invention)

Example 1 was repeated with the modifications that 2473 g (18.0 mol) of $PCl_3$ were reacted with 965 g (3.68 mol) of $Ph_3P$ and that 70 g (0.34 mol) of $PCl_5$ (about 100% excess, based on the $P_4$ content, detectable by $^{31}P$-NMR spectroscopy, of the crude mixture in the residence tank 7) were initially introduced into the residence tank 7. The fractionated rectification at 9 to 13 mbar of the $PCl_3$-depleted reaction product withdrawn from the residence tank 7 gave the following substances, in addition to further unreacted $PCl_3$ 1460 g (8.16 mol) of $PhPCl_2$
201 g (0.91 mol) of $Ph_2PCl$
115 g (1.02 mol) of PhCl
<1 g of $P_4$
22.8 g (87 mmol) of $Ph_3P$

EXAMPLE 6

(according to the invention)

Example 1 was repeated with the modifications that 2002 g (14.6 mol) of $PCl_3$ were reacted with 806 g (3.07 mol) of $Ph_3P$ and that 95 g (0.46 mol) of $PCl_5$ (about 150% excess, based on the $P_4$ content, detectable by $^{31}P$-NMR spectroscopy, of the crude mixture in the residence tank 7) were initially introduced into the residence tank 7.

Fractionated rectification at 9 to 13 mbar of the $PCl_3$-depleted reaction product withdrawn from the residence tank 7 gave the following substances, in addition to further unreacted $PCl_3$:

1298 g (7.25 mol) of $PhPCl_2$
214 g (0.97 mol) of $Ph_2PCl$
91.6 g (0.81 mol) of PhCl
<0.1 g of $P_4$
37.0 g (141 mmol) of $Ph_3P$

I claim:

1. A process for the preparation of chlorophenylphosphanes of the formula $$(C_6H_5)_nPCl_{3-n}$$

in which n is 1 or 2, which comprises introducing liquid triphenylphosphane and gaseous phosphorus trichloride in a molar ratio of 1:(3 to 12) at the upper end of a vertically arranged, elongated reaction gone having temperatures of 350° to 650° C. in the reaction zone, transferring the reaction product discharged at the lower end of the reaction zone to a residence zone charged with phosphorus pentachloride, removing excess phosphorus trichloride from the reaction product, via a subsequent fractioning zone, by heating the residence zone with the resultant formation of a $PCl_3$-depleted reaction product, and separating the substances contained in the $PCl_3$-depleted reaction product by fractionated rectification under reduced pressure.

2. The process as claimed in claim 1, wherein the reaction zone is filled at least 50% of its length with a bulk material comprising granular silicon carbide.

3. The process as claimed in claim 1, wherein the silicon carbide of the bulk material has particle sizes of 2 to 8 mm.

4. The process as claimed in claim 1 wherein the reaction zone in the region of the silicon carbide bulk material has temperatures of 500° to 600° C.

5. The process as claimed in claim 1, wherein the reaction zone comprises an electrically heatable silicon/silicon carbide tube.

* * * * *